United States Patent
Morhenn et al.

(10) Patent No.: US 9,731,265 B2
(45) Date of Patent: Aug. 15, 2017

(54) METHOD FOR HANDLING SOLIDS CAPABLE OF DEFLAGRATION

(71) Applicant: BAYER AKTIENGESELLSCHAFT, Leverkusen (DE)

(72) Inventors: Heinrich Morhenn, Köln (DE); Steffen Salg, Berlin (DE)

(73) Assignee: BAYER AKTIENGESELLSCHAFT, Leverkusen (DE)

(*) Notice: Subject to any disclaimer, the term of this patent is extended or adjusted under 35 U.S.C. 154(b) by 0 days.

(21) Appl. No.: 14/773,824

(22) PCT Filed: Mar. 7, 2014

(86) PCT No.: PCT/EP2014/054428
§ 371 (c)(1),
(2) Date: Sep. 9, 2015

(87) PCT Pub. No.: WO2014/139876
PCT Pub. Date: Sep. 18, 2014

(65) Prior Publication Data
US 2016/0023178 A1  Jan. 28, 2016

(30) Foreign Application Priority Data

Mar. 12, 2013 (EP) ..................... 13158676

(51) Int. Cl.
| | | |
|---|---|---|
| *B01J 19/00* | (2006.01) | |
| *F42B 39/14* | (2006.01) | |
| *F42D 5/00* | (2006.01) | |
| *F42D 5/04* | (2006.01) | |
| *C06B 21/00* | (2006.01) | |
| *C07C 245/04* | (2006.01) | |
| *C07C 311/48* | (2006.01) | |

(52) U.S. Cl.
CPC ............ *B01J 19/002* (2013.01); *C06B 21/00* (2013.01); *C07C 245/04* (2013.01); *C07C 311/48* (2013.01); *F42B 39/14* (2013.01); *F42D 5/00* (2013.01); *F42D 5/04* (2013.01); *B01J 2219/00261* (2013.01); *B01J 2219/00263* (2013.01)

(58) Field of Classification Search
CPC ..................................................... B01J 19/002
See application file for complete search history.

(56) References Cited

U.S. PATENT DOCUMENTS

| | | |
|---|---|---|
| 3,063,477 A | 11/1962 | Vogt |
| 4,191,480 A | 3/1980 | Hiorth |
| 4,336,209 A | 6/1982 | Gyldén et al. |
| 4,608,210 A | 8/1986 | Müller et al. |
| 5,268,177 A | 12/1993 | Barnett, Jr. et al. |
| 5,623,168 A | 4/1997 | Fels et al. |
| 6,416,600 B1* | 7/2002 | Clarke ................ F26B 5/065 149/109.6 |
| 2010/0180757 A1 | 7/2010 | Park et al. |
| 2011/0168950 A1 | 7/2011 | Cohen-Arazi et al. |

FOREIGN PATENT DOCUMENTS

| | | |
|---|---|---|
| DE | 695 13 110 T2 | 5/2000 |
| DE | 10 2009 034039 A1 | 7/2010 |

OTHER PUBLICATIONS

International Search Report dated Jun. 16, 2014, mailed Jun. 24, 2015.
English Translation of International Search Report dated Jun. 16, 2014, mailed Jun. 24, 2015.

* cited by examiner

*Primary Examiner* — Joseph Kosack
(74) *Attorney, Agent, or Firm* — McBee Moore Woodward Vanik IP; Susan McBee; David Woodward

(57) ABSTRACT

Method of processing and handling solids and mixtures capable of deflagration, in particular of processing materials capable of deflagration in the chemical and pharmaceutical industry, wherein the processing and handling is carried out in an environment under a reduced pressure of ≤500 mbara and the processing and/or handling comprises one or more process steps selected from the group consisting of filtration, milling, sieving, mixing, homogenization, granulation, compacting, packaging, drying, storage and transport in a transport container and other steps in apparatuses having mechanical internals.

8 Claims, No Drawings

METHOD FOR HANDLING SOLIDS CAPABLE OF DEFLAGRATION

This is a 371 of PCT/EP2014/054428 filed 7 Mar. 2014, which claims foreign priority benefit under 35 U.S.C. 119 of European Patent Application 13158676.0 filed Mar. 12, 2013, the entire contents of which are incorporated herein by reference.

The invention relates to a method of processing and handling solids and mixtures capable of deflagration, in particular of processing materials capable of deflagration in the chemical and pharmaceutical industry, wherein the processing and handling is carried out in an environment under reduced pressure.

BACKGROUND OF THE INVENTION

The German Technical Rule for Plant Safety (TRAS) No. 410 defines deflagration as follows:

"Deflagration is a reaction which can be triggered in a localized fashion in a prescribed amount of material and which propagates automatically in the form of a reaction front from there through the entire amount of material. The propagation velocity of the reaction front is lower than the speed of sound in the material. Large amounts of hot gases can be liberated in deflagration and these are sometimes also combustible. The deflagration velocity also increases with the temperature and generally also with the pressure".

Solids capable of deflagration decompose after local action of a sufficiently strong source of ignition (initiation) even without the presence of atmospheric oxygen. In contrast to a fire or explosion, deflagration cannot be prevented by exclusion of oxygen. The measure of making inert with nitrogen or other inert gases which is known from explosion protection offers no protection against deflagration. Processing under reduced pressure has hitherto not been considered to be a protective measure for the processing and handling of materials capable of deflagration.

Explosions are rapid deflagrations with a sudden increase in pressure and temperature. When the speed of sound is exceeded, a deflagration changes into a detonation.

Materials capable of deflagration are usually organic or inorganic compounds in solid form. In particular, organic compounds having functional groups such as carbon-carbon double and triple bonds, e.g. acetylenes, acetylides, 1,2-dienes; strained ring compounds such as azirines or epoxides, compounds having adjacent N atoms, e.g. azo and diazo compounds, hydrazines, azides, compounds having adjacent O atoms, e.g. peroxides and ozonides, oxygen-nitrogen compounds such as hydroxylamines, nitrates, N-oxides, 1,2-oxalates, nitro and nitroso compounds; halogen-nitrogen compounds such as chloramines and fluoramines, halogen-oxygen compounds such as chlorates, perchlorates, iodosyl compounds; sulphur-oxygen compounds such as sulphonyl halides, sulphonyl cyanides, and compounds having carbon-metal bonds and nitrogen-metal bonds, e.g. Grignard reagents or organolithium compounds can undergo deflagration. However, many other organic compounds without the abovementioned functional groups and many inorganic compounds can be capable of deflagration.

Essentially, all materials having a decomposition enthalpy of greater than or equal to 500 J/g are considered to be potentially capable of deflagration. Materials which have a decomposition enthalpy of 300-500 J/g and are capable of deflagration are also known.

The deflagration capability of a substance has to be determined individually in the particular case.

Various test methods for testing the deflagration behaviour of materials and mixtures are known.

In the UN testing handbook "Transportation of Dangerous Goods, Manual of Tests and Criteria", 5th Revised Edition, 2009, 2 test methods for determining the deflagration capability are described in section 23 (p. 237 ff).

In the test C.1 ("Time/Pressure Test"), 5 g of the substance to be tested are ignited in a pressure vessel having a capacity of about 17 ml. Criteria for the evaluation are attainment of a limit pressure of about 20.7 bar gauge and also the time after ignition in which the limit pressure is reached. (Bar gauge=bar gauge pressure)

The deflagration capability is assessed as follows in the test C.1:
yes, capable of fast deflagration, when the pressure within the pressure vessel increases from 6.90 bar gauge to 20.70 bar gauge in less than 30 seconds after ignition.
yes, capable of slow deflagration, when the pressure within the pressure vessel increases from 6.90 bar gauge to 20.70 bar gauge in 30 seconds or more after ignition,
not capable of deflagration when the limit pressure of 20.70 bar gauge is not reached.

In the test C.2, a sample is introduced into a Dewar vessel having an internal diameter of about 48 mm and a height of 180-200 mm. The mixture is ignited by means of an open flame.

The deflagration capability is assessed as follows in the test C.2:
yes, capable of fast deflagration, when the deflagration velocity is greater than 5 mm/sec.
yes, capable of slow deflagration, when the deflagration velocity is in the range from 0.35 mm/sec to 5 mm/sec.
not capable of deflagration when the deflagration velocity is less than 0.35 mm/sec or the reaction stops before reaching the lower mark.

Overall, a substance is classed as not capable of deflagration when the substance was not classified as "capable of fast deflagration" in the test C.1 and was classified as not capable of deflagration in the test C.2.

A further test for determining the deflagration capability is described in VDI2263-1 (1990, p. 13 ff.).

In the test in accordance with VDI2263-1, a substance is introduced into a glass tube which has a diameter of about 5 cm and is closed at the bottom and in which a plurality of thermocouples are installed radially offset at various heights. After local initiation by means of a glow coil, a glow plug, a microburner or an ignition mixture of lead (IV) oxide and silicon, the propagation of the decomposition is determined. Initiation is effected from above and from the bottom of the bed. If the decomposition spreads in at least one of the experiments (ignition from above and ignition from below), the material is classified as capable of deflagration.

As ignition sources, it is possible to use, as alternative a glow coil, a glow plug, a microburner or an ignition mixture (silicon/lead oxide in a ratio of 3:2). The time of application and the energy input of the ignition sources are not defined further.

In the standard procedure in accordance with VDI2263-1, the deflagration behaviour is measured at ambient temperature pressure. However, it can also be measured at elevated temperature and in a closed vessel.

It is known that many materials decompose without formation of a closed front and also incompletely in the test in accordance with VDI2263-1. Within the bed, there is frequently formation of channels in the interior of which the decomposition progresses while the surrounding material does not decompose. However, such behaviour represents a hazard potential for processing of a material. A person skilled in the art will select the parameters for the testing of the deflagration behaviour of a material or mixture in such a way that the situation during processing is most accurately reproduced. Thus, in the test in accordance with VDI2263-1, a substance will be brought to the temperature at which processing of the substance is also carried out. As regards the source of ignition, it can be assumed that the substance is not capable of deflagration when no propagation of the reaction is observed after 300 seconds of application of the source of ignition at a temperature of >600° C., for example by means of a glow coil or a glow plug, the latter at an energy input of 40 W. In the case of propagation of the reaction, any type of continuation of the decomposition which propagates through the bed should be evaluated as a sign of deflagration behaviour, even when channel formation is present and the bed does not react over its full width to form a decomposition front.

VDI report 975 (1992) page 99 ff, describes a classification of pulverulent materials which pose a deflagration hazard. The materials capable of deflagration are divided into 3 hazard classes. While materials of the hazard class 3 are in principle not allowed to be processed in apparatuses having mechanical internals, materials of the hazard classes 1 and 2 can be processed in apparatuses having mechanical internals subject to particular provisos.

Important criteria for classification into one of the 3 hazard classes is the plug action time, i.e. the time for which the ignition source in the test VDI2263-1 is switched on from when it is first switched on until the decomposition reaction becomes visible. The authors compare the plug action time with the minimum ignition energy in the case of dust explosions. The plug action time can, with a view to processing in a production apparatus, also be interpreted as the period of time for which an ignition source such as a hot starting place or a hot screw can act on the surrounding substance before a noncritical state is reached again by cooling of the starting place or screw or renewal of the environment around the hot place. Thus: "the shorter the plug action time, the easier it is to trigger deflagration". The authors indicate a plug action time of ≤20 seconds as limit value for classification in hazard class 3 and a limit value of >60 seconds as limit value for classification in hazard class 1.

The production of solids capable of deflagration is carried out using the conventional process steps known from organic and inorganic chemistry. Starting materials are usually reacted with one another in liquid form or in the form of solutions, and the desired material usually precipitates as solid. This is then separated off from the remaining liquid components and is, after further possible purification steps, drying and temporary storage, available in the desired form for packaging and transport to the users. The desired material is optionally processed further and, for example, milled and/or mixed with other components.

The production of solids capable of deflagration is generally unproblematic on the laboratory scale. The amounts handles are small, the probability of initiation of deflagration is low, any deflagration occurring is quickly recognized and even in the case of nonrecognition and propagation of deflagration, the degree of damage is small.

However, the production of materials capable of deflagration is problematical in the case of relatively large amounts as are encountered in a pilot plant operation or production operation. Here, a series of apparatuses, which each have potential initiation sources and in the case of which deflagration can sometimes only be detected a relatively long time after initiation, are used.

Apparatuses in pilot plants and production operations are frequently equipped with mechanical devices which serve for transport, mixing, renewal of the surface or other purposes.

Thus, for example, mixers having moving mechanical elements, for example ploughshare mixers or screw mixers, are used for the homogenization of solids. It is known that the mechanical devices are one of the most frequent causes of initiation of deflagration. Thus, in the case of a malfunction, a moving mixing element can come into direct contact with the wall of the apparatus and local heating occurs at the point of friction and this heating can induce the surrounding material to decompose and thus initiate deflagration. Cases in which a foreign body, for example a screw, has got into an apparatus, got between the wall and stirring/mixing element there and triggered deflagration as a result of heating are likewise known. Even rubbing of hard crusts or friction in a blocked transport screw has resulted in triggering of deflagrations. It is also known that deflagrations can be transferred from one apparatus to the other. Thus, a screw which has been introduced into a mixer can be heated by friction in the manner described. The hot screw is then discharged, for example, into a silo without mechanical internals. The temperature of the screw can still be sufficiently high to induce the surrounding substance to decompose in the silo and thus trigger deflagration. In the same way, agglomerates in which deflagrative decomposition has been triggered can be discharged into an apparatus without mechanical internals and there initiate the deflagrative decomposition of the contents of the apparatus.

A series of measures which allow safe processing of materials capable of deflagration are known.

VDI report 975 (1992), page 99 ff, sets out a methodology for assessing and selecting measures in the processing of pulverulent materials which represent a deflagration hazard. The report describes classification of the materials capable of deflagration into 3 hazard classes, with materials in the hazard class 3 having the highest hazard potential and materials in the hazard class 1 having the lowest hazard potential. Various processing methods are indicated according to the hazard class. Although the criteria mentioned in the said publication do not have general validity, the methodology set out in this publication represents a good starting point for assessing and processing materials capable of deflagration. Examples of safe processing of materials capable of deflagration may also be found in the VDI report 1272 (1996), page 441 ff. In the case of materials having a high deflagration tendency, it is ensured that processing is carried out without mechanical action. This is achieved, for example, by drying being carried out on individual trays in a drying oven rather than in a dryer having mechanical internals, for example a paddle dryer. However, processing without mechanical devices is very complicated. The transport of material frequently has to be carried out manually, which can lead not only to high costs but also to hazards to the health of the operating personnel and to quality problems. Processing without mechanical devices will come into question only when safe processing using mechanical devices is not possible. For example, in the above-cited publication in the VDI report 975 (1992), page 99 ff, only processing methods without mechanical devices are allowed for the materials of hazard class 3.

In the case of materials for which the hazard potential posed by deflagration is less pronounced, mechanical devices can also be used for processing subject to particular conditions. In the cited publication in the VDI report 975 (1992), page 99 ff, this applies to materials in hazard classes 1 and 2.

One customary method of avoiding deflagration is the careful avoidance of introduction of foreign bodies. This can, for example, be effected by removal of metal before introduction in the apparatus so as to prevent the carrying-through of screws and other metallic foreign bodies into the processing step.

Even in the construction of the apparatuses, attention can be paid to avoidance of possible ignition sources, for example by selecting large spacings between a mechanical mixer and the wall.

The abovementioned methods of avoiding sources of ignition can significantly reduce the risk of deflagration, but deflagration can also be ruled out thereby. The methods mentioned are also complicated and in some cases associated with an impairment of the performance of the apparatuses.

A further possible way of avoiding deflagration is to mix the substance capable of deflagration with a further substance which is not capable of deflagration and does not have catalytic activity. A disadvantage of this measure is that the desired substance cannot be obtained with the desired composition. The reduction in the deflagration capability by addition of a further substance is described, for example, in U.S. Pat. No. 5,268,177.

A further method of safely processing substances capable of deflagration is to safely release the pressure arising in a deflagration or safely discharge the gases formed in the deflagration. This can, for example, be achieved by installation of appropriately dimensioned bursting discs and appropriate discharge devices. It has to be noted here that the deflagration velocity increases with increasing pressure, and actuation pressure and discharge line have to be designed accordingly. It also has been noted that entrained substances have to be hindered from propagating the deflagration. This can, for example, be achieved by introducing the discharge gases into a water bath.

A further known method of safely processing substances capable of deflagration is to recognize the commencement of deflagration in good time and suppress the incipient deflagration by removal of the energy. Recognition can be achieved via a series of indicators. For example, the monitoring of temperature and/or pressure is known. However, detection can also be effected via occurrence of particular decomposition gases such as carbon monoxide. When the trigger value has been reached, the energy is removed from the system. In general, this is effected by addition of a relatively large amount of water. The deflagrating substance is cooled to temperatures below the decomposition temperature by the heat capacity of the water. Additional removal of heat can be effected by the formation of water vapour. A detergent can be added to the water in order to ensure good wetting of the deflagrating substance.

A disadvantage of the abovementioned method is that they act only to limit damage and become effective only after triggering of the deflagration. These methods thus lead to loss of at least part of the substance, since the latter partly decomposes and the undecomposed proportions are generally made unusable by water and other reagents. The safe removal of water vapour formed is also problematical.

It can be stated that the methods described hitherto for processing substances capable of deflagration have disadvantages.

It was therefore an object of the present invention to provide better measures for processing and/or handling solids or solid mixtures capable of deflagration. In particular, these measures should reduce the probability of triggering of deflagration without altering the materials properties by addition of a further material.

SUMMARY OF THE INVENTION

The object is achieved by a method in which the processing and/or handling of the solids capable of deflagration is carried out in an environment under reduced pressure. It has surprisingly been found that the triggering of deflagration during the processing and handling of materials capable of deflagration can be significantly delayed in an environment under reduced pressure.

A delay in the triggering of deflagration can surprisingly be achieved by even a slight reduction of the pressure within the apparatus below ambient pressure/atmospheric pressure. Thus, a significant delay was found in the case of a reduction in the pressure within the vessel to less than or equal to 800 mbara (bara=bar absolute). The processing and handling is preferably carried out at a very low pressure within the apparatus. For the processing, preference is given to a pressure range of ≤500 mbara, particularly preferably a pressure range ≤100 mbara, particularly preferably a pressure range ≤20 mbara. For economic and technical reasons, ≥2 mbara, preferably ≥10 mbara, is recommended as lower limit of the pressure range within the vessel.

The method of the invention can be employed for the processing and handling of solid substances capable of deflagration, including explosive solid substances.

DETAILED DESCRIPTION

For the purposes of the present invention, substances capable of deflagration are all substances which either are classified as capable of deflagration in accordance with the UN testing handbook "Transportation of Dangerous Goods, Manual of Tests and Criteria", 5th Revised Edition, 2009, Deflagration, under criteria specified in section 23.2.2 (question "Can it propagate a deflagration?"—answer "Yes, rapidly" or "Yes, slowly"), and/or display spontaneous decomposition in the test VDI2263-1 on testing at the temperature envisaged during processing and ignition from above or below by means of a priming cap, ignition coil or glow plug, the latter with a power uptake of at least 40 W and an application time of 300 seconds, with the decomposition being able to propagate in the form of a decomposition front or in the form of decomposition channels.

Typical materials capable of deflagration for the purposes of the present invention are organic compounds having functional groups such as carbon-carbon double and triple bonds, e.g. acetylenes, acetylides, 1,2-dienes; strained ring compounds such as azirines or epoxides, compounds having adjacent N atoms, e.g. azo and diazo compounds, hydrazines, azides, compounds having adjacent O atoms, e.g. peroxides and ozonides, oxygen-nitrogen compounds such as hydroxylamines, nitrates, N-oxides, 1,2-oxalates, nitro and nitroso compounds; halogen-nitrogen compounds such as chloramines and fluoramines, halogen-oxygen compounds such as chlorates, perchlorates, iodosyl compounds; sulphur-oxygen compounds such as sulphonyl halides, sulphonyl cyanides and compounds having carbon-metal bonds and nitrogen-metal bonds, e.g. Grignard reagents or organolithium compounds. Solids capable of deflagration are materials capable of deflagration in solid form, with the solid being pure or mixed in solid form, e.g. is present as powder or granular material in any particle size. For the purposes of the present invention solids capable of deflagration also include liquids capable of deflagration which are resorbed on solids which are not capable of deflagration and are thus present in solid form. Solids capable of deflagration for the purposes of the present invention likewise include materials capable of deflagration in solid form which have residues of water or other liquids such as solvents (moist solids). The particle size and the particle size distribution are known to have an influence on the deflagration behaviour, but the two parameters do not constitute a restriction of the present invention.

In the experiments carried out (see Examples 1 to 4) in accordance with VDI2263-1, the ignition times or plug action times were increased by a factor of from 2 to 8 by application of a reduced pressure. According to the criteria specified in the VDI report 975 (1992), page 99 ff, the probability of deflagration being able to be triggered decreases when the ignition times or plug action times are increased. Under reduced pressure, solids capable of deflagration become less capable of deflagration according to the abovementioned categorizations, which in turn makes the use of, in particular, apparatuses having mechanical internals possible with a decreased deflagration risk.

Processing and handling for the purposes of the present patent application are process and handling steps for the production, processing, storage and transport of solids capable of deflagration, in particular filtration, drying, milling, sieving, mixing, homogenization, granulation, compacting, packaging, storage and transport in a transport container and also mechanical transport such as transport in transport screws or by means of star feeders. For the purposes of the invention, these process steps can be carried out either in or with the aid of apparatuses in which the solid being processed is moved by means of mechanical devices, for example in a ploughshare mixer, or in or with the aid of apparatuses without mechanical devices, for example silos. The method is particularly advantageous for processing and handling solids capable of deflagration in apparatuses having mechanical internals. Processing, storing and transport in or with the aid of apparatuses without mechanical internals under reduced pressure in order to reduce the risk of explosion of explosive solids or for protection against damage by atmospheric oxygen is known from the prior art. However, the reduced pressure is associated with the provision of an inert atmosphere.

Drying under reduced pressure is also generally known. However, here the reduced pressure accelerates strain and is not used for reducing the deflagration and explosion risk of solids capable of deflagration and explosion.

The surprising decrease in the deflagration and explosion risk of solids capable of deflagration and explosion occurs, in contrast to the prior art for handling explosive mixtures, regardless of whether the processing and/or handling is carried out under an inert atmosphere.

The invention accordingly provides a method of processing and/or handling solids capable of deflagration, which comprises one or more process steps from the group consisting of filtration, milling, sieving, mixing, homogenization, granulation, compacting, packaging, drying, storage and transport in a transport container and other steps in apparatuses having mechanical internals, characterized in that the processing and/or handling is carried out in an environment under reduced pressure.

The reduction of the pressure in the apparatuses is effected by techniques known to those skilled in the art using vacuum pumps such as displacement pumps, jet pumps, rotary vane pumps, centrifugal pumps, water ring pumps, rotary piston pumps and other apparatuses suitable for generating the desired pressure.

In the production of materials capable of deflagration, use is frequently made of mixers having mechanical internals, for example ploughshare mixers or screw mixers ("Nauta mixers") for homogenization or mixing-in of additives. The mixers are generally operated at atmospheric pressure. Comminution tools ("choppers") are sometimes additionally installed in such mixers. A malfunction, for example deformation of the mixing element or introduction of a screw, can result in friction and thus local heating which can trigger deflagration. If such a mixer is operated under reduced pressure instead of atmospheric pressure in an apparatus, the probability of initiation of deflagration can be greatly reduced, the risk of uncontrolled decomposition of the contents of the apparatus decreases and the safety of the plant is significantly increased.

Filtration in a flat-bed filter is a further application for the improvement effected by the measure according to the invention. In a flat-bed filter, a suspension is generally applied to a screen or other filter medium. The filtrate travels under the action of gravity through the screen or filter medium, and the filtration rate can be increased by means of subatmospheric pressure on the filtrate side and/or superatmospheric pressure on the addition side. To homogenize the filtration and the filter cake, the suspension is generally stirred by means of a stirrer. As long as liquid is present on the addition side, the risk of deflagration is low. After the liquid phase has been separated off, the risk of deflagration increases. Mechanical internals, for example the stirrer, can in the case of malfunction lead to heat of friction and thus triggering of deflagration. According to the invention, the filter cake is kept under reduced pressure. This can be achieved, for example, by application of a slightly subatmospheric pressure on the addition side of, for example, 500 mbara at a greater subatmospheric pressure of, for example, 20 mbara on the filtrate side, with a pressure difference across the filter being maintained. It is likewise possible according to the invention to bring the apparatus on the input side or even the entire apparatus to a pressure according to the invention below atmospheric pressure toward the end or after completion of the filtration and before switching on the mechanical devices such as stirrers. In an alternative procedure, the stirrer is switched on while liquid phases are present on the filter, the stirrer is switched off when the liquid level drops in order to avoid triggering of deflagration and the stirrer is switched on again only after a subatmospheric pressure according to the invention has been generated.

Discharge from a flat-bed filter is generally carried out by means of a mechanical discharge device. It can be effected, for example, by means of the stirrer which, for the purposes of discharge, is run in the opposite direction of rotation, or a separate mechanical discharge device. In the case of a malfunction, a deflagration can be triggered by heat of friction. According to the invention, discharge from a flat-bed filter is effected at a pressure below atmospheric pressure, as a result of which the probability of deflagration occurring is significantly reduced.

The transport of materials capable of deflagration by means of transport screws or star feeders is a further application for the improvement effected by the measure according to the invention.

The transport of solids is frequently carried out by means of transport screws which are installed in a tube or tube-like apparatus. Friction of the screw on the wall, or introduction of a foreign body such as a fastening screw into the transport screw, can result in heat of friction and thus triggering of deflagration. Cases in which deflagrations have been triggered by compression in a block transport screw are also known. According to the invention, the pressure in the apparatus surrounding the transport screw is reduced to a pressure below atmospheric pressure, as a result of which the probability of deflagration occurring is significantly reduced.

Star feeders are frequently used at the transition from one apparatus to another apparatus. Friction of the star wheel on the wall, or introduction of a foreign body such as a fastening screw into the star feeder, can cause heat of friction and thus triggering of deflagration. According to the invention, the pressure in the star feeder is reduced to a pressure below atmospheric pressure, as a result of which the probability of deflagration occurring is significantly reduced.

The abovementioned transport screws or star feeders or else other transport techniques convey materials capable of deflagration into apparatuses without mechanical internals, for example buffer vessels, silos, transport containers or other containers.

Deflagration can also be triggered in apparatuses without mechanical devices by introduced hot foreign bodies, for example a fastening screw heated by friction in a transport screw. According to the invention, these apparatuses are maintained at a pressure below atmospheric pressure during and after charging, as a result of which the probability of deflagration occurring is significantly reduced.

A particular problem in the processing of materials capable of deflagration is comminution and milling. In mills, crushes and analogous comminution devices, mechanical energy is introduced into the material being milled and heating by friction occurs even during correct operation and this can trigger deflagration. Introduction of a foreign body such as a screw increases the probability of triggering of a deflagration significantly. According to the invention, the mill or the comminution device is operated at a pressure below atmospheric pressure, as a result of which the probability of deflagration occurring is significantly reduced. The mills or comminution devices can be known mills such as roller crushers, spiked roller crushers or toothed roller crushers.

In sieving and rubber sieving or passing sieving, for example by means of a Frewitt sieve, malfunctions can lead to heat of friction and consequently to triggering of deflagration. According to the invention, the sieving or the sieving by means of a rubbing sieve or passing sieve is carried out at a pressure below atmospheric pressure, as a result of which the probability of deflagration occurring is significantly reduced.

In the drying of solids, these are generally moved by means of mechanical internals in order to continually renew the surface and thus improve mass transfer and heat transport. Typical dryers are, for example, paddle dryers or plate dryers. Some of the flat-bed filters described above are also equipped so that a drying step can follow filtration in these apparatuses. As a result of a malfunction, for example deformation of the mixing element or introduction of a fastening screw, friction can lead to local heating which can trigger deflagration.

Drying can also be carried out in apparatuses without mechanical internals, for example in a fluidized-bed dryer. In such apparatuses, too, introduction of foreign bodies can under unfavourable circumstances lead to deflagration, for example as a result of malfunction of a mechanical rake in the feed region.

Drying is generally carried out with a hot gas, for example hot air or hot nitrogen, being passed through the dryer (=by means of gas convection flows). The hot gases effect both energy input for vaporization and transport of the material. The introduction of energy can also be effected by heating of the wall or by means of heated internals. Drying can also be carried out under reduced pressure rather than in a stream of gas. The influence of a reduced pressure on the deflagration tendency has hitherto not been known/examined, so that other criteria such as the boiling point of the solvent or the melting point of the substance to be dried were used as a basis for the decision as to whether to carry out drying under reduced pressure. According to the invention, the drying of materials capable of deflagration is always carried out under reduced pressure. Setting of the reduced pressure can be effected solely by generation of the subatmospheric pressure by means of a pump or by generation of the subatmospheric pressure by means of a pump and simultaneous introduction of a limited amount of gas into the dryer in order to improve transport of the material. Both measures significantly reduce the probability of deflagration occurring.

In a manner analogous to the applications described, it can be expected that safety can also be significantly increased in other apparatuses having mechanical internals when these are operated according to the invention under reduced pressure.

EXAMPLES

The following experiments demonstrate the influence of reduced pressure on the deflagration capability of azodicarbonamide, without being restricted thereto.

Measurements to determine the deflagration behaviour in accordance with VDI 2263 were carried out.

The measurements were carried out in a metal tube having a diameter of 4.8 cm and a height of 13.5 cm. A glow plug of the type 0 250 201 032-4FS from Bosch let into the bottom of the metal tube (testing tube) served as ignition source. The testing tube was in each case filled with 97% azodicarbonamide procured from Sigma-Aldrich. Four 1.5 mm NiCr—Ni wall thermocouples were subsequently inserted centrally into the bed so that the first element was located 1 cm above the tip of the glow plug and the other elements were in each case located 2 cm higher up.

For the measurements, the testing tube was transferred to an autoclave having an internal volume of 4 l and an internal height of 15.5 cm. The testing tube was for this purpose fastened to a rod fixed on the autoclave lid in such a way that the testing tube was not in contact with the wall of the autoclave. Autoclave and sample were at room temperature.

In the autoclave lid, there were gastight lead-throughs for the wires for heating the ignition source and for the thermocouples and a capillary for a pressure sensor installed outside the autoclave and also a valve for evacuating the apparatus or breaking the vacuum in the apparatus.

A measurement commences with the simultaneous supply of electric power and starting of the temperature-time recordings. The power introduced was maintained at a constant 40 W over the duration of the measurement. As point in time for ignition of the material, the temperature rise at the 1$^{st}$ measurement point (1 cm above the ignition source) was evaluated. After commencement of the supply of electric power, the temperature at the 1$^{st}$ measurement point remained virtually constant or rose slowly by a few ° C., and when deflagration commenced a strong temperature rise of ≥5° C./sec was observed.

The increase in the temperatures at the other temperature sensors and the pressure in the autoclave increased in each case with a time offset after commencement of ignition.

Example 1—Azodicarbonamide—Under Atmospheric Pressure

The above-described testing tube was filled with 85 g of azodicarbonamide (ADCA). The testing tube was transferred into the autoclave. The mixture was heated by means of the glow plug with a power introduced over the duration of the measurement of 40 W. After 19 seconds, the temperature at the temperature sensor installed 1 cm above the glow plug increased.

The experiment was repeated twice under identical conditions. The temperature rose after 19 and 15 seconds, respectively.

ADCA thus belongs to hazard class 3 according to the VDI report 975 (1992), page 99 ff. (Not suitable for apparatuses having mechanical internals)

Example 2—Azodicarbonamide—Reduced Pressure of 750 Mbara

The above-described testing tube was filled with 85 g of azodicarbonamide (ADCA). The testing tube was transferred into the autoclave and the autoclave was evacuated to 750 mbara by means of a pump. The mixture was heated by means of the glow plug with a power introduced over the duration of the measurement of 40 W. After 34 seconds, the temperature at the temperature sensor installed 1 cm above the glow plug increased.

The experiment was repeated twice under identical conditions. The temperature rose after 37 and 41 seconds, respectively.

Example 3—Azodicarbonamide—Reduced Pressure of 500 Mbara

The above-described testing tube was filled with 85 g of azodicarbonamide (ADCA). The testing tube was transferred into the autoclave and the autoclave was evacuated to 500 mbara by means of a pump. The mixture was heated by means of the glow plug with a power introduced over the duration of the measurement of 40 W. After 53 seconds, the temperature at the temperature sensor installed 1 cm above the glow plug increased.

The experiment was repeated twice under identical conditions. The temperature rose after 67 and 65 seconds, respectively.

Example 4—Azodicarbonamide—Reduced Pressure of 100 Mbara

The above-described testing tube was filled with 85 g of azodicarbonamide (ADCA). The testing tube was transferred into the autoclave and the autoclave was evacuated to 100 mbara by means of a pump. The mixture was heated by means of the glow plug with a power introduced over the duration of the measurement of 40 W. After 149 seconds, the temperature at the temperature sensor installed 1 cm above the glow plug increased.

The experiment was repeated twice under identical conditions. The temperature rose after 137 and 189 seconds, respectively.

Under the subatmospheric pressure applied, ADCA behaves as a material capable of deflagration in hazard class 1 according to the categorization of the VDI report 975 (1992), page 99 ff. (Processing in apparatuses having mechanical internals possible).

Example 5—Azodicarbonamide—Reduced Pressure of 10 Mbara

The above-described testing tube was filled with 85 g of azodicarbonamide (ADCA). The testing tube was transferred into the autoclave and the autoclave was evacuated to 10 mbara by means of a pump. The mixture was heated by means of the glow plug with a power introduced over the duration of the measurement of 40 W. After 172 seconds, the temperature at the temperature sensor installed 1 cm above the glow plug increased.

The experiment was repeated twice under identical conditions. The temperature rose after 166 and 190 seconds, respectively.

Example 6—Tolyl Fluanide (50%)—Under Atmospheric Pressure

The above-described testing tube was filled with 40 g of a mixture of 50% by weight of tolyl fluanide and 50% by weight of kieselguhr. The testing tube was transferred into the autoclave. The mixture was heated by means of the glow plug with a power introduced over the duration of the measurement of 40 W. After 75 seconds, the temperature at the temperature sensor installed 1 cm above the glow plug increased, and the temperature increase at this temperature sensor reached a maximum of 3.9 K/sec after 170 seconds.

Example 7—Tolyl Fluanide (50%)—Under Reduced Pressure of 100 Mbara

The above-described testing tube was filled with 40 g of a mixture of tolyl fluanide (50%). The testing tube was transferred into the autoclave and the autoclave was evacuated to 100 mbara by means of a pump. The mixture was heated by means of the glow plug with a power introduced over the duration of the measurement of 40 W. After 103 seconds, the temperature at the temperature sensor installed 1 cm above the glow plug increased, and the temperature increase at this temperature sensor reached a maximum of 1.9 K/sec after 240 seconds.

Compared to the measurement at atmospheric pressure, a significant slowing both of the initiation and the propagation of the deflagration is found. For the processing of a mixture of tolyl fluanide (50%), this means that the risk both of triggering and of uncontrolled spread is significantly reduced during processing at a pressure of 100 mbar.

The invention claimed is:
1. Method of processing and/or handling solids and mixtures capable of deflagration, wherein the processing and/or handling is carried out in an environment under a reduced pressure of ≤500 mbara and the processing and/or handling comprises one or more process step selected from the group consisting of filtration, milling, sieving, mixing, homogenization, granulation, compacting, packaging, drying, storage and transport in a transport container and other steps in apparatuses having mechanical internals.

2. Method according to claim 1, wherein the process step is transport in transport screws or by means of star feeders.

3. Method according to claim 1, wherein the process step is carried out in a ploughshare mixer, screw mixer or another mixer having mechanical mixing and/or chopping tools.

4. Method according to claim 1, wherein the process step is carried out in a flat-bed filter, an oscillating sieve, a rotational sieve and/or another filtration or sieving device having mechanical tools.

5. Method according to claim 1, wherein the process step is carried out in a roller crusher, spiked roller crusher or toothed roller crusher mill or another comminution apparatus.

6. Method according to claim 1, wherein the process step is carried out in a paddle dryer, plate dryer or fluidized-bed dryer.

7. Method according to claim 1, wherein storage or intermediate buffering is carried out in containers without mechanical tools.

8. Method according to claim 1, wherein transport is carried out in a transport container.

* * * * *